(12) United States Patent
Akiyama et al.

(10) Patent No.: US 10,401,214 B2
(45) Date of Patent: Sep. 3, 2019

(54) PROBE, OBJECT INFORMATION ACQUISITION APPARATUS, AND METHOD OF MANUFACTURING THE PROBE

(71) Applicant: CANON KABUSHIKI KAISHA, Tokyo (JP)

(72) Inventors: Takahiro Akiyama, Kawasaki (JP); Yoshio Hotta, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 179 days.

(21) Appl. No.: 15/450,841

(22) Filed: Mar. 6, 2017

(65) Prior Publication Data

US 2017/0176396 A1 Jun. 22, 2017

Related U.S. Application Data

(63) Continuation of application No. 14/052,351, filed on Oct. 11, 2013, now Pat. No. 9,618,386.

(30) Foreign Application Priority Data

Oct. 12, 2012 (JP) .................................. 2012-226898

(51) Int. Cl.
| | |
|---|---|
| *G01H 9/00* | (2006.01) |
| *G01N 29/24* | (2006.01) |
| *A61B 5/00* | (2006.01) |
| *G01N 21/17* | (2006.01) |
| *A61B 8/00* | (2006.01) |

(52) U.S. Cl.
CPC .............. *G01H 9/00* (2013.01); *A61B 5/0095* (2013.01); *A61B 8/4209* (2013.01); *A61B 8/4236* (2013.01); *G01N 21/1702* (2013.01); *G01N 29/2406* (2013.01); *G01N 29/2418* (2013.01); *G01N 2021/1706* (2013.01); *G01N 2291/0427* (2013.01); *Y10T 156/10* (2015.01)

(58) Field of Classification Search
CPC ...... G01H 9/00; A61B 5/0095; A61B 8/4209; A61B 8/4236; G10K 11/02; G01N 21/1702; G01N 29/2406; G01N 29/2418; G01N 2021/1706; G01N 2291/0427; Y10T 156/10
USPC ........... 73/655, 632; 310/322, 324, 334, 336
See application file for complete search history.

(56) References Cited

U.S. PATENT DOCUMENTS

| | | | | |
|---|---|---|---|---|
| 2010/0210949 A1* | 8/2010 | Habu | ....................... | A61B 8/00 600/459 |
| 2011/0108838 A1* | 5/2011 | Kageyama | ............ | B06B 1/0292 257/49 |
| 2012/0253196 A1* | 10/2012 | Nagata | ................. | A61B 8/5292 600/443 |

* cited by examiner

*Primary Examiner* — Natalie Huls
*Assistant Examiner* — Suman K Nath
(74) *Attorney, Agent, or Firm* — Canon U.S.A. Inc., IP Division

(57) ABSTRACT

A probe configured to receive an acoustic wave from an object including an element having a cell structure, in which a vibration membrane having one of a pair of electrodes formed with a gap arranged therebetween is supported so that the vibration membrane can be vibrated by the acoustic wave; a light reflection layer provided at a position near the object with respect to the element and configured to reflect light; and a support layer provided between the element and the light reflection layer and configured to support the light reflection layer.

28 Claims, 4 Drawing Sheets

PROBE, OBJECT INFORMATION ACQUISITION APPARATUS, AND METHOD OF MANUFACTURING THE PROBE

CROSS-REFERENCE TO RELATED APPLICATIONS

This application is a continuation of U.S. patent application Ser. No. 14/052,351 filed Oct. 11, 2013, which claims the benefit of Japanese Patent Application No. 2012-226898 filed Oct. 12, 2012, each of which is hereby incorporated by reference herein in their entirety.

BACKGROUND

Field

Aspects of the present invention generally relate to a probe that receives an acoustic wave generated from an object, an object information acquisition apparatus, and a method of manufacturing the probe.

Description of the Related Art

One of optical imaging techniques may be a photoacoustic imaging technique called photoacoustic tomography (PAT). The photoacoustic imaging is a technique that detects an acoustic wave (also called "photoacoustic wave") generated because of irradiation with light, and generates image data from an obtained receive signal. This photoacoustic wave is generated when an object is irradiated with pulsed light from a light source, and a tissue which has absorbed the energy of the light propagating in the object is vibrated. The wavelength of this acoustic wave depends on the size of the tissue, and is typically in a wavelength range of ultrasonic waves.

Japanese Patent Laid-Open No. 2010-075681 suggests a probe including an element that receives such an acoustic wave. In the photoacoustic imaging, if the light for generating the acoustic wave is incident on a receive surface of the element in the probe, an acoustic wave is generated at the receive surface, and the generated acoustic wave may cause noise. To restrict the acoustic wave generated at the receive surface, the probe described in Japanese Patent Laid-Open No. 2010-075681 has a light reflection layer directly on the receive surface of the element in the probe so that the light is not incident on the receive surface.

Also, a capacitive micromachined ultrasonic transducer (CMUT) manufactured by using a micromachining technique is studied as a substitute of a piezoelectric element. CMUT is a transducer including a capacitive element. CMUT can transmit and receive an acoustic wave such as an ultrasonic wave by using vibration of a vibration membrane. CMUT can obtain a good broadband characteristic particularly in liquid.

In the capacitive transducer, an acoustic wave may be generated when irradiation light for generating an acoustic wave is incident on a receive surface of an element, and the acoustic wave may cause noise. However, if the light reflection layer is arranged directly on the element like Japanese Patent Laid-Open No. 2010-075681, a stress of the light reflection layer may cause a change in spring constant of a vibration membrane forming the element, a variation in deformation of the vibration membrane, and the like. The influence on the vibration membrane may cause a decrease and a variation in sensitivity of the element, and a decrease in bandwidth.

SUMMARY

Aspects of the present invention generally relate to a light reflection layer while restricting the influence of the light reflection layer on an element.

According to an aspect of the invention, a probe configured to receive an acoustic wave from an object includes an element having a cell structure, in which a vibration membrane having one of a pair of electrodes formed with a gap arranged therebetween is supported so that the vibration membrane can be vibrated by the acoustic wave, a light reflection layer provided at a position near the object with respect to the element and configured to reflect light, and a support layer provided between the element and the light reflection layer and configured to support the light reflection layer. The support layer has a rupture stress of 50 MPa or larger.

Further features of the present disclosure will become apparent from the following description of exemplary embodiments with reference to the attached drawings.

DESCRIPTION OF THE EMBODIMENTS

An exemplary embodiment is described below with reference to the drawings.

Figure 1:
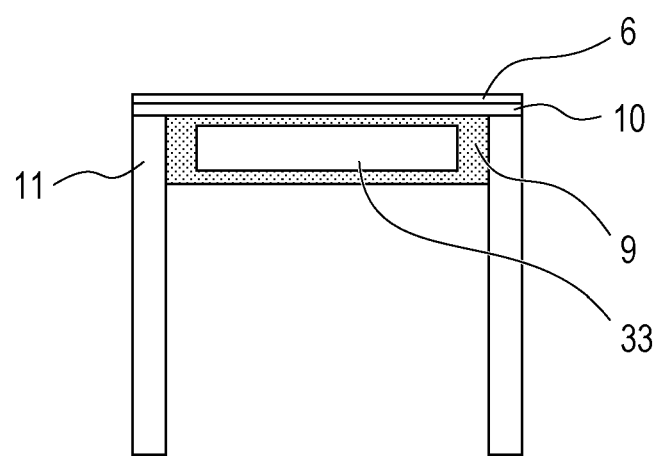
FIG. 1 is a cross-sectional view showing an example of a configuration of a probe.

FIG. 1 is a cross-sectional view showing an example of a configuration of a probe. The probe of this embodiment includes at least a capacitive transducer 33 which is an electromechanical transducer, a support layer 10, and a light reflection layer 6. FIG. 1 illustrates a desirable example of this embodiment. An acoustic matching layer 9 is provided between the capacitive transducer 33 and the support layer 10. Also, the capacitive transducer 33 is housed in a housing frame 11 serving as a housing, and members such as a flexible substrate are not illustrated. First, the capacitive transducer 33 is explained with reference to FIGS. 2A and 2B.

Capacitive Transducer

Figure 2A:
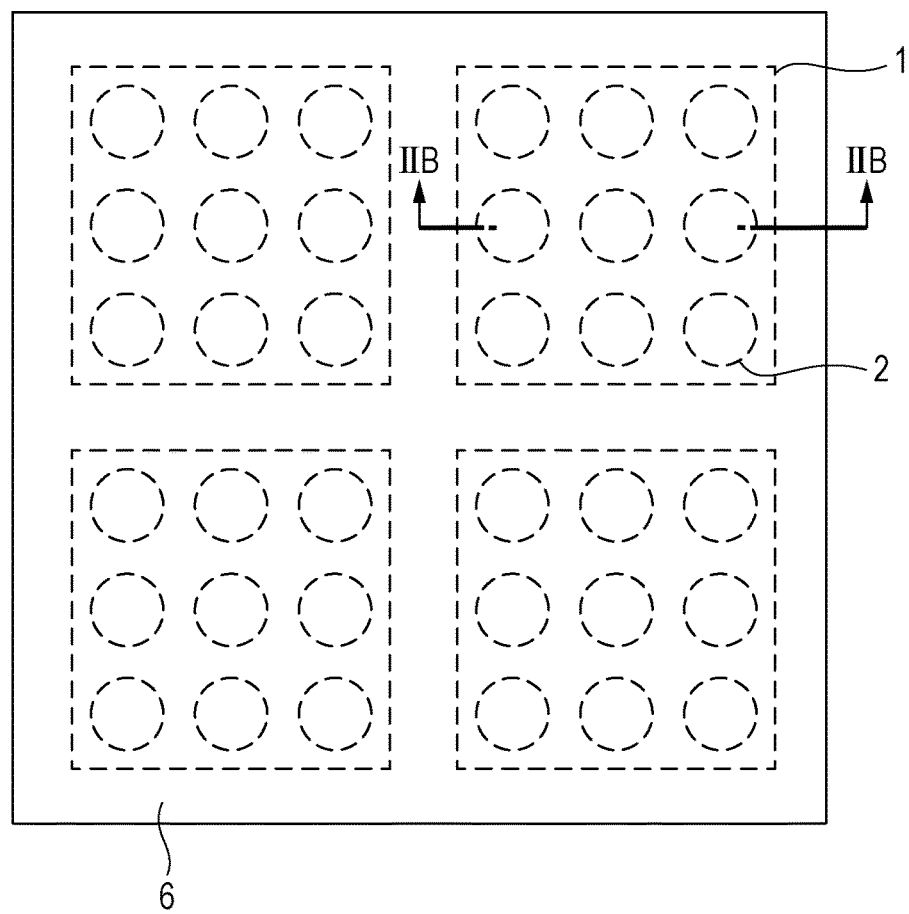
FIGS. 2A and 2B are schematic illustrations showing an example of a configuration of a capacitive transducer.
Figure 2B:
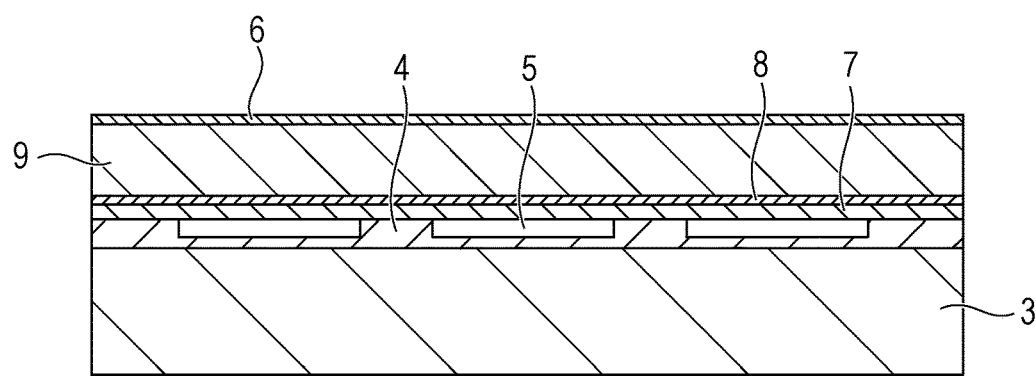

FIG. 2A is a top view of the capacitive transducer 33. FIG. 2B is a cross-sectional view taken along line IIB-IIB in FIG. 2A. The capacitive transducer 33 includes at least one element 1 having at least one cell structure 2. The cell structure 2 has a pair of electrodes formed with a gap arranged therebetween, and supports a vibration membrane having one of the pair of electrodes so that the vibration membrane can be vibrated. FIG. 2A illustrates only four elements 1; however, the number of elements may be any number. Also, each element 1 includes nine cell structures 2; however, the number of cell structures 2 may be any number. The shape of the cell structure is a circle in FIG. 2A; however, the shape may be a quadrangle, a hexagon, or other shape.

In FIG. 2B, a substrate 3 uses a semiconductor substrate such as a silicon substrate. The substrate 3 functions as a first electrode. Alternatively, a layer made of metal etc. may be provided on a substrate, and may serve as the first electrode.

A gap 5 is present between the substrate 3 serving as the first electrode, and a second electrode 8. A support part 4 is formed on the substrate 3. The support part 4 supports the second electrode 8 and a vibration membrane 7 so that the second electrode 8 and the vibration membrane 7 can be vibrated.

In FIG. 2B, the vibration membrane 7 is, for example, single crystal silicon. If the vibration membrane 7 is low-resistance single crystal silicon, the single crystal silicon may be used as a second electrode. In this case, metal serving as the second electrode 8 may not be arranged. The vibration membrane 7 may be an insulating film, such as a silicon nitride film or a silicon oxide film.

The substrate 3 serving as the first electrode faces the second electrode 8. A voltage is applied from a voltage applying unit (not shown) to an area between the pair of electrodes. Also, the element 1 can acquire an electric signal of each element from the second electrode 8 by using a wiring line. That is, the first electrode serves as a common electrode in which the elements are electrically connected through the first electrode, and the second electrode 8 serves as a signal acquiring electrode that acquires an electric signal of each element. However, if first electrodes are electrically separated for respective elements, the second electrode 8 may serve as a common electrode, and each first electrode may serve as a signal acquiring electrode that acquires an electric signal of each element.

Principle of Driving

The principle of driving of the capacitive transducer according to the present embodiment is described. When an acoustic wave is received, the voltage applying unit applies a direct voltage to the first electrode so that a potential difference is generated between the first electrode and the second electrode 8. When the acoustic wave is received, the vibration membrane 7 in which the second electrode 8 is formed is bent. Hence, the interval between the second electrode 8 and the first electrode (the distance in the depth direction of the gap 5) is changed, and the capacitance is changed. As the result of the change in capacitance, current is output from the second electrode 8. A current-voltage converter (not shown) converts the current into a voltage, and provides a receive signal of an acoustic wave. As described above, by changing the configuration of the wiring line, a direct voltage may be applied to the second electrode 8 and an electric signal of each element may be acquired from the first electrode.

Also, the capacitive transducer of this embodiment can transmit an acoustic wave. If an acoustic wave is transmitted, a direct voltage is applied to the first electrode, an alternative voltage is applied to the second electrode 8, and the vibration membrane 7 with the second electrode 8 formed is vibrated by an electrostatic force. With this vibration, an acoustic wave can be transmitted. Even if an acoustic wave is transmitted, by changing the configuration of the wiring line, a direct voltage may be applied to the second electrode 8, an alternating voltage may be applied to the first electrode, and the vibration membrane 7 may be vibrated.

Acoustic Matching Layer 9

As shown in FIG. 1, in the probe of this embodiment, the acoustic matching layer 9 is located above the vibration membrane 7 (at an object side) of the capacitive transducer 33. The acoustic matching layer 9 may have an acoustic impedance which is close to the acoustic impedance of the vibration membrane 7. To be more specific, the acoustic impedance may be preferably in a range from 1 MRayls to 2 MRayls. The acoustic matching layer 9 may be silicone rubber in which organic polymer containing polydimethylsiloxane (PDMS) as a main constituent is bridged. Alternatively, PDMS with silica particles etc. added, or fluorosilicone in which fluorine is substituted for part of hydrogen of PDMS may be used. Silicone rubber less affects the vibration membrane 7, and may preferably have a thickness in a range from 10 μm to 900 μm. Also, not to largely change mechanical properties, such as the deformation and the spring constant of the vibration membrane 7, the Young's modulus of the acoustic matching layer 9 may be preferably 10 MPa or smaller. In the case of silicone rubber in which organic polymer containing polydimethylsiloxane (PDMS) as a main constituent is bridged, the Young's modulus is about 1 MPa.

As described above, since the acoustic matching layer 9 has a small Young's modulus, if the light reflection layer 6 is directly formed on the acoustic matching layer 9, the film stress of the acoustic matching layer 9 may affect, for example, deform the light reflection layer 6. Hence, in this embodiment, the light reflection layer 6 is formed through the support layer 10.

Support Layer 10

The support layer 10 may have a larger Young's modulus than the Young's modulus of the acoustic matching layer 9 to restrict bending and deformation of the light reflection layer 6. To be more specific, the Young's modulus of the support layer 10 may be preferably in a range from 100 MPa to 20 GPa. Also, the support layer 10 may have an acoustic impedance which is close to the acoustic impedance of the acoustic matching layer 9. To be more specific, the acoustic impedance may be preferably in a range from 1 MRayls to 5 MRayls.

A film with an acoustic impedance close to the acoustic impedance of the acoustic matching layer 9 may be an olefin film of polymethylpentene, polyethylene, etc. However, such an olefin film tends to be easily ripped if a flaw or the like is made, and hence the olefin film may have difficulty in handling.

Owing to this, the support layer 10 of the light reflection layer 6 may have a sufficient rigidity (in particular, a sufficient rapture stress), in addition to that acoustic-wave reflection is small at the interface with respect to the acoustic matching layer 9. To be more specific, the support layer 10 of this embodiment has a rapture stress of 50 MPa or larger. With such a rapture stress, the support layer 10 is hardly ripped. Further, as described above, the Young's modulus may be preferably large in addition to that the rapture stress is large. To be more specific, the Young's modulus may be preferably in a range from 100 MPa to 20 GPa.

If the probe is used while being in contact with a specific acoustic medium (acoustic matching solution), the solubility parameter (the SP value) of the support layer 10 may be preferably apart by 5 or more from the solubility parameter of the acoustic medium. That is, the difference between the solubility parameter of the support layer 10 and the solubility parameter of the acoustic medium may be preferably 5 or more. The solubility parameter is an index of solubility indicative of the amount by which a certain substance is solved in another certain substance. If the acoustic medium immerses in the light reflection layer 6 through a flaw made in the light reflection layer 6 and contacts the support layer 10, the immersion of the acoustic medium may cause the support layer 10 to be ruptured. If the solubility parameter of the support layer 10 is apart by 5 or more from the solubility parameter of the acoustic medium, the resistance against the acoustic medium is high.

A material suitable for the support layer 10 arranged on the acoustic matching layer 9 may be polyester, such as polyethylene terephthalate or polyethylene naphthalate, polyimide, polycarbonate, nylon, or polyethersulfone. In particular, polyester is the most preferable material. A polyester film has a rapture stress larger than 80 MPa, has a Young's modulus larger than 1 GPa, and has a sufficient rigidity (in particular, a sufficient rupture stress). Also, the polyester film has good surface smoothness, and is good for a support base member for the light reflection layer 6. It is to be noted that polyester has a large acoustic impedance although polyester has a high rigidity. However, if the thickness of the polyester film is a certain thickness or smaller (the detail will be described later), a decrease in transmissivity of the acoustic wave can be restricted. If the acoustic medium uses castor oil, since the castor oil has a solubility parameter of 16.2 and the polyester film has a solubility parameter of 10.7, the polyester film has a sufficient resistance to the castor oil. Now, the thickness of the polyester film and the decrease in transmissivity of the photoacoustic wave are described.

The polyester film has an acoustic impedance of 2.9 Mrayls. The intensity of the acoustic wave is decreased when the acoustic wave reaches the vibration membrane 7 because of reflection etc. at the interface between the acoustic matching layer 9 and the support layer 10 formed of the polyester film. At this time, the intensity of the acoustic wave transmitted to the vibration membrane 7 depends on the thickness of the polyester film. It is assumed that the sonic speed (the propagation speed of the acoustic wave) in the polyester film is 2260 m/s.

If the probe is in the liquid of the acoustic medium, it is assumed that the acoustic impedance of the liquid of the acoustic medium is 1.3 Mrayls. The acoustic medium may be castor oil, olive oil, glycerol, or glycol ether, or a mixture of these materials. Also, if the acoustic matching layer 9 uses PDMS, it is assumed that PDMS has an acoustic impedance of 1.5 Mrayls, and a sonic speed of 1000 m/s. The mechanical impedance of the vibration membrane 7 depends on the frequency (the number of vibrations of the vibration membrane). In many cases, the mechanical impedance of the vibration membrane 7 is equivalent to or smaller than the mechanical impedance of the acoustic medium.

Under this conditions, if the polyester film has a thickness of 30 µm or smaller, the decrease in transmissivity of the acoustic wave with the polyester film as the support layer 10 is 10% or lower in a frequency range from 1 MHz to 5 MHz, and 15% or lower in a frequency range from 1 MHz to 8 MHz with respect to the case without the polyester film.

In contrast, if the polyester film has a large thickness of 40 µm, the decrease in transmissivity of the acoustic wave with the polyester film is 13% in the frequency range from 1 MHz to 5 MHz, and 19% in the frequency range from 1 MHz to 8 MHz with respect to the case without the polyester film. Hence, it is found that if the thickness of the polyester film is increased, the transmissivity of the acoustic wave is decreased. Accordingly, in this embodiment, if the support layer 10 uses the polyester film, the thickness may be preferably 30 µm or smaller.

Light Reflection Layer 6

The light reflection layer 6 of this embodiment is a member that restricts incidence of light on the element 1. To be more specific, the member reflects illumination light on an object or diffused light of the illumination light. If a diagnosis is made for a living body such as a breast as an object, in many cases, a near-infrared region with wavelengths in a range from 700 nm to 1000 nm is used as laser light. The light reflection layer 6 may have a high reflectivity (preferably a reflectivity of 80% or higher, or more preferably, a reflectivity of 90% or higher) for light in a use wavelength range (for example, 700 nm to 1000 nm). To be more specific, the light reflection layer 6 may be preferably formed of a metal thin film, and may use metal containing at least one element of Au, Ag, Al, and Cu, or an alloy of these elements.

Also, the light reflection layer 6 may preferably have a film thickness of 150 nm or larger. If the film thickness is 150 nm or layer, a sufficient reflectivity can be obtained. However, with regard to the acoustic impedance, the film thickness may be preferably 10 µm or smaller. For example, in case of Au, the acoustic impedance of Au is as high as about $63 \times 10^6$ [kg·m$^{-2}$·s$^{-1}$], the film thickness has to be small by certain degrees to prevent reflection of the acoustic wave because of mismatching between acoustic impedances. Hence, in case of Au, the film thickness may be preferably 1/30 or smaller of the wavelength of the acoustic wave in the material. In particular, a receive band of the acoustic wave generated by the photoacoustic effect is typically about 10 MHz. With regard to that the wavelength in water with 10 MHz is about 150 µm, the Au film may preferably have a thickness of 5 µm or smaller. Vapor deposition or sputtering may be used as the formation method. Also, to increase the adhesion, a base layer of Cr or Ti may be provided.

Alternatively, the light reflection layer 6 may not use a metal film, and may use a dielectric multilayer film. Still alternatively, a laminated structure in which a dielectric multilayer film is formed on a metal film may be used. The laminated structure is desirable because the reflectivity can be further increased.

Arrangement of Support Layer 10 at Housing

Figure 3:
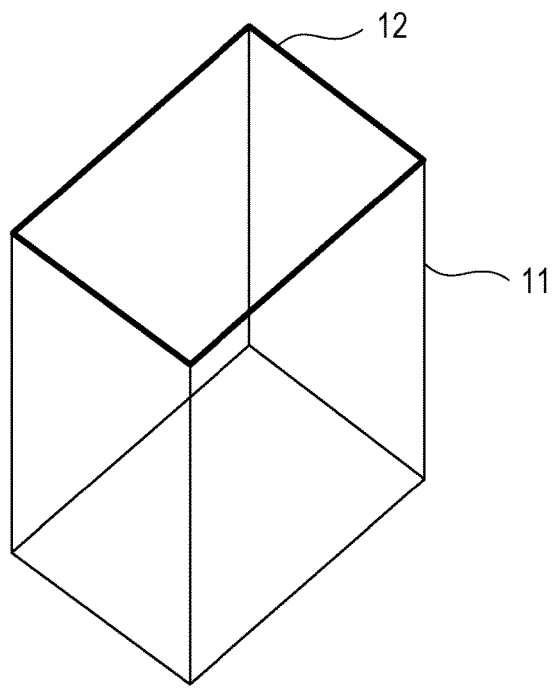
FIG. 3 is a perspective view showing an example of a housing of the probe.

FIG. 3 is a schematic illustration showing a distal end portion of the housing frame 11 serving as a housing that houses the capacitive transducer therein. In many cases, the housing frame 11 of the probe is formed of metal or an alloy, and the material may be aluminum, SUS, etc.; however, the material may be other material such as ceramic. The light reflection layer 6 may be arranged to be flat with respect to a surface of the probe near the object (a surface of the probe facing the object). If the flatness of the light reflection layer 6 is decreased, the thickness of the acoustic matching layer 9 arranged between the surface of the element and the light reflection layer 6 becomes not uniform. Hence, the interface reflection condition of the photoacoustic wave becomes not uniform, possibly causing a factor of disturbing the acoustic wave to be received, such as interference of multiple reflection or a decreased in receive intensity. Therefore, the light reflection layer 6 is may be arranged at the housing so as not to decrease the flatness of the light reflection layer 6.

The light reflection layer 6 may be previously formed on a film which becomes the support layer 10. An adhesive is applied on an upper end surface 12 of the housing frame 11, then the support layer 10 with the light reflection layer 6 formed on the upper end surface 12 is arranged, and the adhesive is hardened by heat while a pressure is applied to the support layer 10. Thus, the support layer 10 is bonded to the upper end surface 12. Hence, the support layer 10 such as the polyester film may preferably have a thermal contraction of 1.2% or higher. The polyester film or the like used for the support layer 10 is processed by drawing in the manufacturing process thereof, and the thermal contraction characteristic varies mainly depending on the drawing condition. The thermal contraction is a contraction when a film is held at a certain temperature and then is returned at a room temperature.

Herein, Table shows the results when polyester films with different thermal contractions were actually prepared and were bonded on upper end surfaces 12.

TABLE

| Heat contraction (%) | Flatness after bonding |
| --- | --- |
| 5 | Good |
| 2.2 | Good |
| 1.2 | Good |
| 0.8 | Fair |
| 0.5 | Bad |

The thermal contraction when each polyester film was put at a temperature of 150° C. for 30 minutes and then was returned at a room temperature (20° C.) was used. The housing frame 11 used a frame made of aluminum. The result of flatness after bonding is a result based on visual check. The bonding temperature is 120° C. Referring to the results of the polyester films in Table, when each film used as the support layer 10 is fixed to the housing frame 11 by the adhesive, the difference between the thermal expansion coefficient of the housing frame 11 and the thermal expansion coefficient of the film is not absorbed by the contraction of the film, the flatness is decreased. That is, if a film with a small thermal contraction is used, a proper tension is not applied to the film surface after bonding, the surface may be wavy, and it is difficult to mount the film as a flat film surface. The housing frame 11 uses aluminum and the film uses the polyester film in the above-described example, the difference in thermal expansion varies depending on the material and the quality of the material of the member used as the housing frame 11, and the material etc. of the film used as the support layer 10. However, even if aluminum, which has a large thermal expansion among metal, is used for the housing frame, as long as a film has a thermal contraction of 1.2% or higher like the polyester film, the film may likely have flatness. Hence, if a material with a thermal contraction of 1.2% or higher is used for a film serving as the support layer 10 of this embodiment, the film can be bonded to the housing frame 11 with a proper tension.

The adhesive used in this embodiment may be any adhesive as long as the film, which becomes the support layer 10, and the housing frame 11 can be bonded to each other. However, it is desirable that the adhesive does not have a high thermosetting temperature. To be more specific, the thermosetting temperature may be preferably in a range from 80° C. to 120° C. In particular, a silicone adhesive is suitable because the silicone adhesive is likely bonded to the polyester film and the metal of the housing frame 11. The setting temperature may be in a range from about 80° C. to 120° C.

Manufacturing Method

Next, a method of manufacturing the probe of this embodiment is described in detail. First, the light reflection layer 6 is formed on the film which becomes the support layer 10. If the light reflection layer 6 uses a metal thin film, the light reflection layer 6 may be formed on the film serving as the support layer 10, for example, by vapor deposition or sputtering. If Au is used, the adhesion may be weak. In this case, a Cr film may be formed as a base layer, and then an Au film may be formed. Also, surface processing such as ozone asher may be provided. Alternatively, the metal thin film may not be used, and multiple dielectric layers of oxide films such as $TiO_2$ may be formed on a film.

Then, the support layer 10 with the light reflection layer 6 formed at the housing frame 11 is bonded. The support layer 10 may occasionally receive a stress or the like of the light reflection layer 6. To provide the light reflection layer 6 in a flat state at the probe, a proper tension may be applied to the support layer 10. The support layer 10, which is heated and contracted, is brought into contact with the housing frame 11 with a pressure, and in the pressed state, the adhesive is hardened by heat. Accordingly, the state with a proper tension can be provided. The part to which the support layer 10 is bonded is an end surface of the frame that defines the external shape of the housing frame 11. The housing frame 11 desirably has a small thickness to make the entire probe compact; however, desirably has a frame area for bonding. The frame thickness of the housing frame 11 may be determined with regard to both the thickness and the area. To be more specific, the frame thickness may be preferably in a range from 100 μm to 10 mm.

To be more specific, the support layer 10 may be bonded to the housing frame 11 by the following method. For the housing frame 11, the example bonding method for the housing frame 11 made of SUS is described. However, even with other material, bonding may be provided by properly selecting an adhesive. First, the upper end surface 12 of the housing frame 11 is wiped and cleaned with an organic solvent, and then a primer is applied to the end surface. The primer is low-viscosity liquid to allow the surface to be easily bonded. The primer suitable for the kind of the adhesive may be used. The primer is applied to the upper end surface 12, the solvent is volatilized, and then thermal processing for fixing is performed. Then, the adhesive is applied to the upper end surface 12. The adhesive to be used may be desirably a silicone adhesive; however, may use an epoxy adhesive or an acryl adhesive.

Then, the support layer 10 with the light reflection layer 6 formed is temporarily fixed to a flat plate, the bonding surface of the support layer 10 is pressed to the upper end surface 12 of the housing frame 11 with the adhesive applied, and thermosetting processing is performed in the pressed and fixed state. The support layer 10 such as the polyester film is contracted in a setting process, and hence is bonded and fixed with a proper tension. Accordingly, even if the temperature is returned at the room temperature, the flat light reflection layer 6 can be formed.

Then, in the state in which the light reflection layer 6 is attached to the housing frame 11, the inside of the housing is filled with an acoustic matching agent, which becomes the acoustic matching layer 9. The acoustic matching agent may be silicone rubber in which organic polymer containing polydimethylsiloxane (PDMS) as a main constituent is bridged. Alternatively, PDMS with silica particles etc. added, or fluorosilicone in which fluorine is substituted for part of hydrogen of PDMS, may be used. The inside of the housing is filled with the organic polymer by dropping the organic polymer before the organic polymer is bridged. The filling amount may be determined so that the substrate 3, in which the element 1 to be inserted next is formed, is sufficiently embedded in the organic polymer. After the organic polymer is added, vacuum deairing processing is performed. This is for removing air bubbles caught during filling or air bubbles originally contained in the organic polymer.

Figure 4:
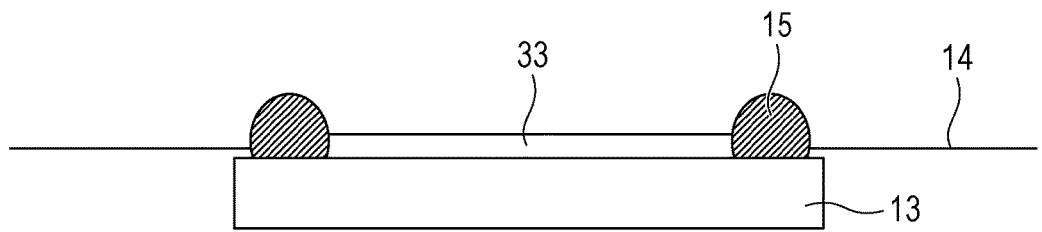
FIG. 4 is a schematic illustration showing an example of connection between the capacitive transducer and a flexible substrate.

Then, the capacitive transducer 33 is inserted into the housing. FIG. 4 is a schematic illustration showing an example of connection between the capacitive transducer 33 and a flexible substrate 14. The substrate 3 with the element 1 formed is fixed to a device board 13. The device board 13 may use a glass epoxy substrate etc. At an end portion of the device board 13, an electrode terminal of the capacitive transducer and the flexible substrate 14 are connected by wire bonding, and a bonding part is sealed with a sealing part 15. Electric connection is not limited to the connection by wire bonding, and may be provided by an anisotropic conductive film (ACF) etc.

Figure 5:
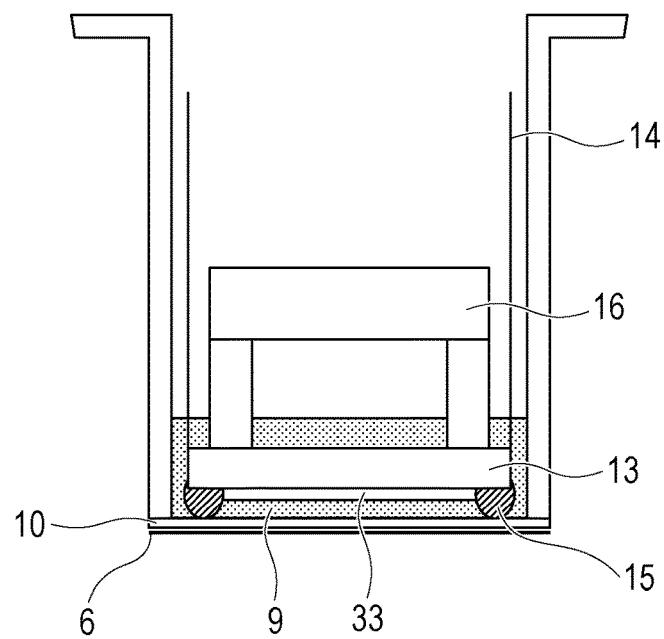
FIG. 5 is a cross-sectional view showing an example of insertion of the capacitive transducer into the housing.

As described above, the capacitive transducer 33 connected with the flexible substrate 14 is inserted into the housing, which is filled with the acoustic matching agent. FIG. 5 is a schematic illustration showing an example of insertion of the capacitive transducer 33 into the housing. The capacitive transducer 33 is inserted into the housing from a side of a surface with the element 1 formed. At this time, not to catch air bubbles, the capacitive transducer 33 is pushed at a sufficiently low speed, so that the capacitive transducer 33 is embedded in the acoustic matching agent. The thickness of a part, which becomes the acoustic matching layer 9, is determined in accordance with the distance between the receive surface of the capacitive transducer 33 and the support layer 10 bonded to the housing frame 11. Hence, the pushing amount of the receive surface may be monitored during the insertion, so as to prevent generation of an inclination. To be more specific, to prevent the generation of an inclination, the device board 13 may be pushed at a plurality of points by using a pressure jig 16.

In this way, when the embedment of the capacitive transducer 33 into the organic polymer, which is the acoustic matching agent, is ended, the housing container is inserted into an oven while the embedment part of the housing container is arranged at the lower side in the gravity direction. The setting conditions are determined in accordance with the temperature and the holding time. The conditions are more desirable for the process if the holding time is increased whereas the setting temperature is not increased. In case of PDMS, the setting temperature is selected within a range from 80° C. to 120° C., and the holding time is selected within a range from 3 hours to 24 hours.

The probe thus formed includes the acoustic matching layer 9 on the vibration membrane 7 of the element 1 arranged at the receive surface of the probe, the support layer 10 is formed thereon, and the light reflection layer 6 is formed thereon. Accordingly, the support layer 10 supports the light reflection layer 6, and the stress of the light reflection layer 6 does not so affect the acoustic matching layer 9 or the vibration membrane 7. Accordingly, deformation etc. of the vibration membrane 7 hardly occurs, and although the light reflection layer 6 is arranged, a variation in performance of the probe is restricted, and the acoustic wave can be received in a good state.

Object Information Acquisition Apparatus

The probe described in the above-described embodiment may be applied to an object information acquisition apparatus that receives an acoustic wave. The capacitive transducer 33 in the probe receives an acoustic wave from an object. By using an electric signal output from the capacitive transducer 33, information about the inside of the object, in which an optical characteristic of the object such as an optical absorption coefficient is reflected, can be obtained.

Figure 6:
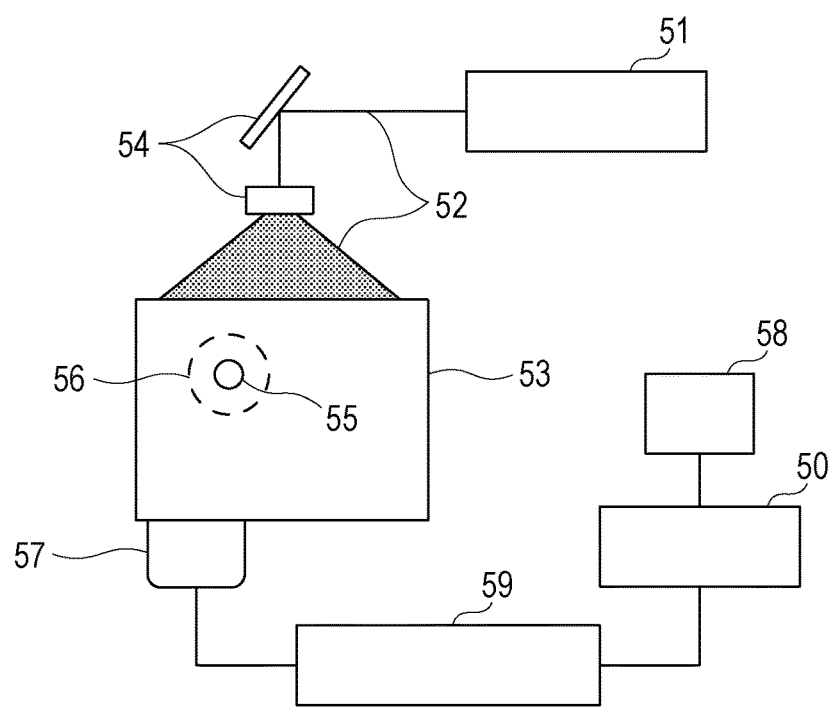
FIG. 6 is a schematic illustration of an object information acquisition apparatus including the probe.

FIG. 6 illustrates the object information acquisition apparatus using a photoacoustic effect. An object 53 is irradiated with pulsed light 52 generated from a light source 51 through optical members 54, such as a lens, a mirror, and an optical fiber. An optical absorber 55 arranged in the object 53 absorbs the energy of the pulsed light, and generates an acoustic wave 56. A probe 57 receives the acoustic wave 56 and converts the acoustic wave 56 into an electric signal. The probe 57 outputs the converted electric signal to a signal processor 59. The signal processor 59 performs signal processing, such as A/D conversion and amplification, on the input electric signal, and outputs the processed signal to a data processor 50. The data processor 50 acquires object information (object information in which the optical characteristic of the object such as the optical absorption coefficient is reflected) as image data by using the input signal. A display 58 displays an image based on the image data input from the data processor 50. The probe may provide mechanical scanning, or may be moved by a user, such as a doctor or a technician, relative to the object (hand-held type).

Example 1

Example 1 is described below as an example of a method of manufacturing a probe. The housing frame 11 of the probe was formed of SUS. The support layer 10 used a polyethylene terephthalate film with a thickness of 12 μm (lumirror-F-65 manufactured by Toray Industries, Inc.). A laminated film of a contact layer formed of a 10-nm Cr film and a 150-nm Au film was formed by vapor deposition, to provide the light reflection layer 6. The attachment of the support layer 10 to the housing frame 11 was performed as follows.

First, the upper end surface 12 (see FIG. 3) was wiped and cleaned with the organic solvent, and hence oil and dusts were removed. Then, to ensure the bonding strength of the silicone adhesive, the dedicated primer No. 4 is applied on the end surface. The primer No. 4 is a silicone-resin-dedicated primer manufactured by Shin-Etsu Chemical Co., Ltd., and is for ensuring the bonding strength between the silicone adhesive and SUS. The primer was applied to the upper end surface 12 of the SUS frame, and thermal processing was performed in the oven at 80° C. for 30 minutes for volatilizing and fixing the solvent.

Then, the silicone adhesive was applied, and hence the polyester film was bonded. The adhesive used X-32-949 manufactured by Shin-Etsu Chemical Co., Ltd. Fine particles were mixed in the adhesive. The mixing was performed by adding the sphericel-60P18 manufactured by Potters-Ballotini Co., Ltd., by 5 parts per hundred parts of resin (phr), performing sufficient stirring and mixing, and performing centrifugal deairing.

The adhesive was applied by transferring. Transfer is a method of filling a recess having a predetermined film thickness with the adhesive by a just full amount, and transferring the filling on the upper end surface 12 of the SUS frame. The film thickness of the adhesive was from 50 μm to 200 μm.

Then, the polyester film was attached. First, the polyester film was temporarily fixed to a plate made of metal and having a flat surface so that the bonding surface faces the SUS frame. The temporary fixture may be performed by using an adhesive tape or the like, so that the film is not loosened. Then, the plate was brought into contact with the SUS frame end surface. The plate is held with a pressure at the SUS frame by using the weight of the plate or a spring etc., and the adhesive is hardened by heat while the plate is held. The thermosetting condition was at 120° C. for 60 minutes. The polyester film after the adhesive is hardened by heat is bonded and fixed in a flat state.

Then, the housing container in the state, in which the support layer 10 with the light reflection layer 6 formed was arranged, was filled with PDMS, which becomes the acoustic matching layer 9. PDMS (X-32-1619 manufactured by Shin-Etsu Chemical Co., Ltd) was dropped into the SUS frame housing container directly from a tube. In this example, dropping was performed by a depth of about 5 mm.

Then, air bubbles caught during dropping and air bubbles contained in PDMS were removed by vacuum deairing processing. To be more specific, PDMS was left for 30 minutes or longer in vacuum of $5\times10^{-2}$ Torr or less.

Then, the capacitive transducer 33 was embedded in PDMS dropped in the SUS frame housing container. As shown in FIG. 4, the capacitive transducer 33 was fixed to the device board 13 made of glass epoxy. The thus mounted capacitive transducer 33 was pushed and embedded slowly while the surface of the capacitive transducer near the vibration membrane 7 faced the polyester film surface so as not to catch air bubbles. The distance between the capacitive transducer 33 and the polyester is calculated from a pressing amount. Also, the device board 13 was pushed at a plurality of points by using the pressure jig 16 shown in FIG. 5 so as not to be inclined.

In this way, the device board 13 is pressed substantially until the top of the sealing part 15 by wire bonding contacts the polyester surface. The film thickness of PDMS of the acoustic matching layer 9 formed by the method of this example is determined in accordance with the height of the sealing part 15. In this example, the film thickness of the acoustic matching layer 9 was in a range from 300 μm to 500 μm. Then, the SUS frame housing container was put into the oven in the state in which the capacitive transducer 33 was embedded so that the support layer 10 faces the lower side and the surface of the light reflection layer 6 does not contact any part to maintain a hollow condition. The setting conditions were at 80° C. for 15 hours.

The probe formed as described above has the light reflection layer 6 with good flatness on the support layer 10. The variation in performance can be restricted, and a photoacoustic wave can be received in a good state.

Since the support layer is provided between the element and the light reflection layer, even if the light reflection layer is provided, the influence on the vibration membrane of the element can be reduced.

While the present disclosure has been described with reference to exemplary embodiments, it is to be understood that these embodiments are not limiting. The scope of the following claims is to be accorded the broadest interpretation so as to encompass all such modifications and equivalent structures and functions.

What is claimed is:

1. A probe configured to receive an acoustic wave from an object, the probe comprising:
    a capacitive element having a cell structure, in which a vibration membrane having one of a pair of electrodes formed with a gap arranged therebetween is supported so that the vibration membrane is vibratable by the acoustic wave;
    a light reflection layer provided closer to the object than the capacitive element and configured to reflect light;
    a support layer provided between the capacitive element and the light reflection layer and configured to support the light reflection layer; and
    an acoustic matching layer provided between the capacitive element and the support layer,
    wherein the support layer has a rupture stress of 50 MPa or larger, and the acoustic matching layer has a smaller acoustic impedance than an acoustic impedance of the support layer.

2. The probe according to claim 1, wherein the support layer contacts the light reflection layer to support the light reflection layer.

3. The probe according to claim 1, wherein a difference between a solubility parameter of the acoustic matching layer and a solubility parameter of an acoustic medium that contacts the probe is greater than or equal to 5.

4. The probe according to claim 1, wherein the support layer has a larger Young's modulus than a Young's modulus of the acoustic matching layer.

5. The probe according to claim 4, wherein the support layer has a larger Young's modulus than a Young's modulus of the acoustic matching layer so that the light reflection layer is not easily bent.

6. The probe according to claim 1, wherein the support layer has an acoustic impedance in a range from 1 MRayls to 5 MRayls.

7. The probe according to claim 1, wherein the support layer has a Young's modulus in a range from 100 MPa to 20 GPa.

8. The probe according to claim 1, wherein the acoustic matching layer has an acoustic impedance in a range from 1 MRayls to 2 MRayls.

9. The probe according to claim 1, wherein the acoustic matching layer has a Young's modulus of 10 MPa or smaller.

10. The probe according to claim 1, wherein the support layer has a thickness of 30 μm or smaller.

11. The probe according to claim 1, further comprising:
    a housing configured to house the capacitive element,
    wherein the support layer has a thermal contraction of 1.2% or higher, and the support layer is bonded to the housing.

12. The probe according to claim 1, wherein the support layer is made of polyester.

13. The probe according to claim 12, wherein the polyester is polyethylene terephthalate.

14. The probe according to claim 1, wherein the light reflection layer is formed of a metal thin film containing at least one element of Au, Ag, Al, and Cu.

15. The probe according to claim 1, wherein the light reflection layer is formed of a dielectric multilayer film.

16. The probe according to claim 1, wherein the acoustic matching layer has a thickness in a range from 10 μm to 900 μm.

17. The probe according to claim 1, wherein the acoustic matching layer has a smaller acoustic impedance than an acoustic impedance of the support layer so that reflection caused by a difference between the support layer and the capacitive element in acoustic impedance of the acoustic wave incident on the support layer is reduced.

18. The probe according to claim 1, wherein the support layer extends outward beyond a range where the acoustic matching layer is provided to support the light reflection layer.

19. A probe configured to receive an acoustic wave from an object, the probe comprising:
    a capacitive element having a cell structure, in which a vibration membrane having one of a pair of electrodes formed with a gap arranged therebetween is supported so that the vibration membrane is vibratable by the acoustic wave;
    a light reflection layer provided closer to the object than the capacitive element and configured to reflect light;
    a support layer provided between the capacitive element and the light reflection layer and configured to support the light reflection layer; and
    an acoustic matching layer provided between the capacitive element and the support layer,
    wherein the support layer has a larger Young's modulus than a Young's modulus of the acoustic matching layer, and the acoustic matching layer has a smaller acoustic impedance than an acoustic impedance of the support layer.

20. The probe according to claim 19, wherein the support layer has an acoustic impedance in a range from 1 MRayls to 5 MRayls.

21. The probe according to claim 19, wherein the support layer has a Young's modulus in a range from 100 MPa to 20 GPa.

22. The probe according to claim 19, wherein the acoustic matching layer has an acoustic impedance in a range from 1 MRayls to 2 MRayls.

23. The probe according to claim 19, wherein the acoustic matching layer has a Young's modulus of 10 MPa or smaller.

24. The probe according to claim 19, wherein the support layer has a thickness of 30 μm or smaller.

25. The probe according to claim 19, wherein the support layer has a larger Young's modulus than a Young's modulus of the acoustic matching layer so that the light reflection layer is not easily bent.

26. The probe according to claim 19, wherein the acoustic matching layer has a smaller acoustic impedance than an acoustic impedance of the support layer so that reflection caused by a difference between the support layer and the capacitive element in acoustic impedance of the acoustic wave incident on the support layer is reduced.

27. An object information acquisition apparatus, comprising:
the probe according to claim 1;
a light source; and
a data processor,
wherein the probe receives an acoustic wave generated by irradiating an object with light from the light source and converts the acoustic wave into an electric signal, and
wherein the data processor acquires information about an inside of the object using the electric signal.

28. A probe configured to receive an acoustic wave from an object, the probe comprising:
a capacitive element having a cell structure, in which a vibration membrane having one of a pair of electrodes formed with a gap arranged therebetween is supported so that the vibration membrane is vibratable by the acoustic wave;
a light reflection layer provided closer to the object than the capacitive element and configured to reflect light;
a support layer provided between the capacitive element and the light reflection layer and configured to support the light reflection layer; and
an acoustic matching layer provided between the capacitive element and the support layer,
wherein a difference between a solubility parameter of the acoustic matching layer and a solubility parameter of an acoustic medium that contacts the probe is greater than or equal to 5.

* * * * *